(12) United States Patent
Brubaker et al.

(10) Patent No.: US 11,515,002 B2
(45) Date of Patent: Nov. 29, 2022

(54) METHODS AND SYSTEMS FOR 3D STRUCTURE ESTIMATION

(71) Applicant: THE GOVERNING COUNCIL OF THE UNIVERSITY OF TORONTO, Toronto (CA)

(72) Inventors: Marcus Anthony Brubaker, Toronto (CA); Ali Punjani, Toronto (CA); David James Fleet, Toronto (CA)

( * ) Notice: Subject to any disclaimer, the term of this patent is extended or adjusted under 35 U.S.C. 154(b) by 946 days.

(21) Appl. No.: 16/288,429

(22) Filed: Feb. 28, 2019

(65) Prior Publication Data

US 2020/0066371 A1 Feb. 27, 2020

Related U.S. Application Data

(63) Continuation of application No. 15/292,520, filed on Oct. 13, 2016, now Pat. No. 10,282,513.

(60) Provisional application No. 62/284,890, filed on Oct. 13, 2015.

(51) Int. Cl.
*G16B 15/00* (2019.01)
(52) U.S. Cl.
CPC .................................. *G16B 15/00* (2019.02)
(58) Field of Classification Search
None
See application file for complete search history.

(56) References Cited

U.S. PATENT DOCUMENTS

2016/0055292 A1 2/2016 White

OTHER PUBLICATIONS

Grigorieff, N. (2007) Frealign: High-resolution refinement of single particle structures. Journal of Structural Biology, 157:117-125.
Le Roux, N. et al. (2012) A Stochastic Gradient Method with an Exponential Convergence Rate for Finite Training Sets. eprint arXiv:1202.6258.
Mindell, J.A. and Grigorieff, N. (2003) Accurate Determination of Local Defocus and Specimen Tilt in Electron Microscopy. Journal of Structural Biology, 142:334-347.
Elmlund, H. et al. (2013) Prime: Probabilistic Initial 3D Model Generation for Single-Particle Cryo-Electron Microscopy. Structure, 21:1299-1306.
Elmund, D. et al. (2012) Simple: Software for ab initio reconstruction of heterogeneous single-particles. Journal of Structural Biology, 190:420-427.
Scheres, S.H.W. (2012) A Bayesian View on Cryo-EM Structure Determination. Journal of Molecular Biology, 415:406-418.
Saff, E.B. and Kujilaars, A.B.J. (1997) Distributing many points on a sphere. The Mathematical Intelligencer, 19:5-11.
Office Action for U.S. Appl. No. 15/292,520; USPTO; dated May 24, 2017.
Scheres, S.H.W. Journal of Structural Biology, 2012, 180, 519-530.
Tokdar et al. Wiley Interdisciplinary Reviews, 2010, vol. 2, Issue 1, p. 54-60.

*Primary Examiner* — Michael L Borin
(74) *Attorney, Agent, or Firm* — Bhole IP Law; Anil Bhole; Marc Lampert

(57) ABSTRACT

Disclosed herein are systems and methods for efficient 3D structure estimation from images of a transmissive object, including cryo-EM images. The method generally comprises, receiving a set of 2D images of a target specimen from an electron microscope, carrying out a reconstruction technique to determine a likely molecular structure, and outputting the estimated 3D structure of the specimen. The described reconstruction technique comprises: establishing a probabilistic model of the target structure; optimizing using stochastic optimization to determine which structure is most likely; and, optionally utilizing importance sampling to minimize computational burden.

15 Claims, 17 Drawing Sheets

METHODS AND SYSTEMS FOR 3D STRUCTURE ESTIMATION

TECHNICAL FIELD

The following relates generally to 3D structure estimation from particle images.

BACKGROUND

Biological processes occur as the result of binding and chemical interactions between molecules inside cells. The majority of these molecules are protein structures, constructed from 20 different amino acid monomer building blocks. Each different type of protein, coded in DNA, is a unique sequence of these monomers joined into a chain. These chains fold into 3D shapes during construction and it is this final 3D structure that determines the function of the protein. Because function depends on structure, discovering the structures of viruses, proteins and other molecules is fundamental to understanding biological processes, and is an important part of discovering drugs that can inhibit or accelerate the action of specific proteins involved in disease pathways. The ability to expeditiously determine the 3D structure of molecules could thus revolutionize the process of drug development, and accelerate research into key biological processes.

SUMMARY

In one aspect, a method for molecule structure reconstruction from a set of 2D Cryo-electron microscope particle images of at least one target is provided, the method comprising determining a probabilistic model of 3D structures for the at least one target; and optimizing the probabilistic model utilizing Stochastic Gradient Descent to determine a most likely 3D structure of each target.

In another aspect, a system for molecular structure reconstruction is provided, the system comprising: a storage unit for storing a set of 2D Cry-electron microscope particles images of at least one target; a processing unit for executing a method of determining a probabilistic model of 3D structures for the at least one target, and optimizing the probabilistic model utilizing Stochastic Gradient Descent to determine a most likely 3D structure of each target.

These and other aspects are contemplated and described herein. It will be appreciated that the foregoing summary sets out representative aspects of systems and methods to assist skilled readers in understanding the following detailed description.

DESCRIPTION OF THE DRAWINGS

The features of the invention will become more apparent in the following detailed description in which reference is made to the appended drawings wherein.

DETAILED DESCRIPTION

Figure 1:
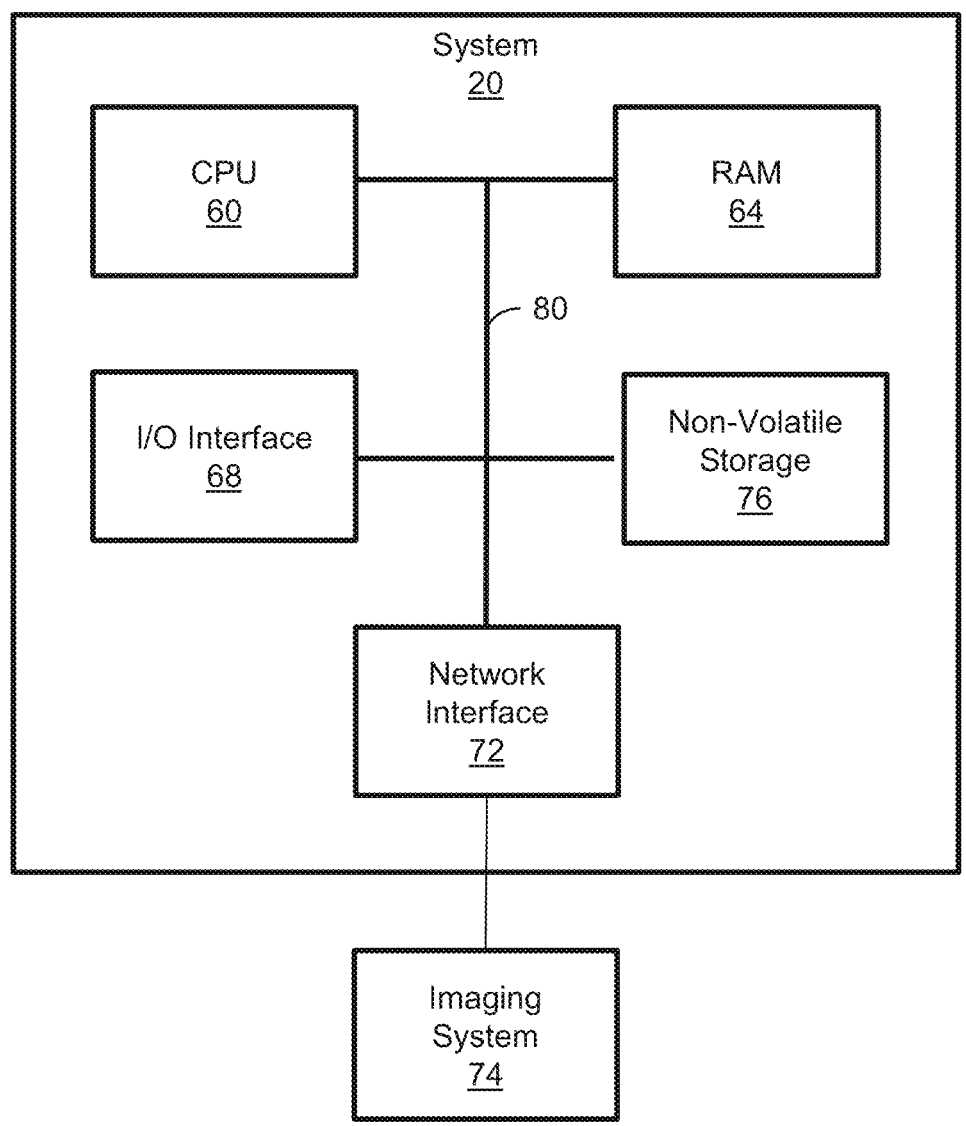
FIG. 1 shows a system for 3D molecular structure estimation.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

Recently, techniques have been developed that attempt to determine 3D structures of proteins, viruses and other molecules from images thereof. Once images of a target molecule are collected, determination of a 3D structure of the molecule requires the sucessful completion of a problematic reconstruction of the 3D structure from the images.

For example, Electron Cryomicroscopy (cryo-EM) is an emerging, computer vision-based approach to 3D macromolecular structure determination. Cryo-EM is applicable to medium to large-sized molecules in their native state. This scope of applicability is in contrast to X-ray crystallography, which requires a crystal of the target molecule, which are often impossible to grow, or nuclear magnetic resonance (NMR) spectroscopy, which is limited to relatively small molecules. Cryo-EM has the potential to unveil the molecular and chemical nature of fundamental biology through the discovery of atomic structures of previously unknown biological structures, many of which have proven difficult or impossible to study by conventional structural biology techniques. As such, Cryo-EM is receiving considerable attention in the life science and structural biology fields.

In cryo-EM, a purified solution of a target molecule is first cryogenically frozen into a thin (single molecule thick) film, and then imaged with a transmission electron microscope. A large number of such samples are obtained, each of which provides a micrograph containing hundreds of visible, individual molecules. In a process known as particle picking, individual molecules are imaged, resulting in a stack of cropped images of the molecule (referred to as particle images). Each particle image provides a noisy view of the molecule with an unknown pose.

Once a large set of 2D electron microscope particle images of the molecule have been obtained, reconstruction is carried out to estimate the 3D density of a target molecule from the images. The ability of cryo-EM to resolve the structures of complex proteins depends on the techniques underlying the reconstruction process. Progress in employing Cryo-EM, and other imaging techniques, to determine 3D structure from images has been hindered by the difficulty of the computational task associated with reconstruction.

The problem addressed during reconstruction is similar to multi-view scene carving and to large-scale, uncalibrated, multi-view reconstruction. Like multi-view scene carving, the goal is to estimate a dense 3D occupancy representation of shape from a set of different views. However, unlike many approaches to scene carving, the 3D poses of the molecule in different images are unknown. Like uncalibrated, multi-view reconstruction, reconstruction uses a large number of uncalibrated views to obtain high fidelity 3D reconstructions. However, the low signal-to-noise levels in cryo-EM particle images (often as low as 0.05) and the different image formation model prevent the use of common feature matching techniques to establish correspondences. Computed Tomography (CT) uses a similar imaging model (orthographic integral projection), however in CT the projection direction of each image is known, whereas with cryo-EM the 3D pose for each particle image is unknown.

Existing reconstruction techniques suffer from two key problems. First, without good initialization, they converge to poor or incorrect solutions, often with little indication that something went wrong. Second, they are extremely slow, which limits the number of particles images one can use to mitigate the effects of noise; this problem is likely to worsen as high-throughput data collection becomes more common, providing larger datasets, and better hardware enables higher resolution images.

Some approaches to density estimation for reconstruction in cryo-EM use a form of iterative refinement based on an initial estimate of the 3D density, they determine the best matching alignment (i.e., 3D pose and image position) for each particle image. A new density estimate is then constructed using the Fourier Slice Theorem, much like CT. In effect, using the 3D pose and position of the particle in each particle image, the new density is found through interpolation and averaging of the observed particle images, often performed in the Fourier domain. However, these approaches are fundamentally limited in several ways. Even if one knew the correct 3D molecular density, the very low signal to noise ratio (SNR) makes it difficult to accurately identify the correct pose and position for each particle image. This problem is exacerbated when the initial density is inaccurate. As a consequence, poor initializations result in estimated structures that are either clearly wrong (see FIG. 16 described below) or, worse, appear plausible but are misleading in reality, yielding incorrect 3D structures. Finally, for the case of density estimation with many particle images, all data are used at each refinement iteration, causing these methods to be extremely slow.

Alternatively, to avoid the need to estimate a single 3D pose and position for each particle image, Bayesian approaches to reconstruction have been proposed in which pose and position for each particle image are treated as latent variables, and then marginalized numerically. Bayesian approaches were originally proposed for 2D image alignment, later for alignment comprising 3D orientation and 2D image position, and have since been used where batch, gradient-based optimization was performed. Nevertheless, due to the computational cost of marginalization, the method was only applied to small numbers of class-average images obtained by clustering, aligning and averaging individual particle images according to their appearance, to reduce noise and the number of particle images used during the optimization. The RELION™ software package uses pose marginalization and a batch Expectation-Maximization algorithm for density estimation. This approach is, however, computationally expensive. The website for the RELION™ software reports that reconstruction from a dataset of 100,000 particle images typically take two weeks on 200 cores.

Disclosed herein are systems and methods for efficient 3D structure estimation from 2D images of a transmissive object, including cryo-EM images produced by a transmission electron microscope.

The method generally comprises, receiving a set of 2D particle images of a target (e.g. from an electron microscope), carrying out a reconstruction technique to determine a likely 3D structure, and outputting the estimated 3D structure of the target. The described reconstruction technique comprises: establishing a probabilistic model of the target structure; optimizing using stochastic optimization to determine which structure is most likely; and, optionally utilizing importance sampling to minimize computational burden.

The described method provides a new framework for reconstruction comprising stochastic optimization techniques to perform maximum-a-posteriori (MAP) density estimation in a probabilistic model rather than batch optimization, permitting applicability to very large datasets. This allows for more efficient optimization, and for robustness to initialization. Further, a Monte-Carlo based importance sampling technique is described that may reduce the cost of evaluating the objective function by orders of magnitude, which is particularly valuable when working at higher resolutions. The framework may be configured to implement a Bayesian technique, which includes marginalizing over all poses of particle images rather than just picking a pose.

The resulting reconstruction technique can be applied to large stacks of images, providing high resolution 3D reconstructions possibly in a shorter period of time than was possible on a workstation having less computational power, and starting from a random initialization. The reconstruction technique is applicable ab-initio, i.e. without prior knowledge or a best guess of the molecular structure to generate 3D structures with resolution of approximately 1 nanometer.

Though described in many instances specifically with respect to Cryo-EM images for simplicity and clarity of illustration, the systems and methods are adaptable to other imaging modalities with necessary modifications. The embodiments are applicable to a range of imaging modalities where reconstruction of a 3D structure is desired from 2D images representing specific poses of a 3D target, which may be a protein, virus or other molecule, or any entity imaged by way of a transmissive imaging modality. Specifically, the embodiments are applicable to images of any transmissive object imaged with a suitable wavelength energy beam, including biological specimens with electron beams, soft tissue with x-ray beams, translucent objects with light, etc.

Furthermore, though described in many instances specifically in the context of the reconstruction of a single 3D structure from each dataset of 2D images, the invention is applicable to the simultaneous reconstruction of multiple 3D structures from each dataset, with each structure representing one of a multitude of different targets present in the dataset.

FIG. 1 shows various physical components of a system 20 for 3D molecular structure estimation. As will be appreciated, while the system 20 is illustrated as being a single physical computer, it can alternatively be two or more computers acting cooperatively to provide the functionality described. As shown, the system 20 has a number of physical and logical components, including a central processing unit (CPU) 60, random access memory (RAM) 64, an input/output (I/O) interface 68, a network interface 72, non-volatile storage 76, and a local bus 80 enabling the CPU 60 to communicate with the other components. The CPU 60 executes an operating system and an application for performing 3D molecular structure estimation. The functionality of the application is described below in greater detail.

The RAM 64 provides relatively responsive volatile storage to the CPU 60. The I/O interface 68 enables an administrator to interact with the system 20 via a keyboard, a mouse, a speaker, and a display. The network interface 72 permits wired or wireless communication with other systems. The non-volatile storage 76 stores computer readable instructions for implementing the operating system and the application for performing 3D molecular structure estimation, as well as any data used by the application. During operation of the system 20, the computer readable instructions for the operating system and the application, and the data may be retrieved from the non-volatile storage 76 and placed in the RAM 64 to facilitate execution. An imaging system 74 may further be linked to the system to obtain images for molecular structure estimation. The imaging system generally comprises one or more electron microscopes, or other suitable devices.

Figure 2:
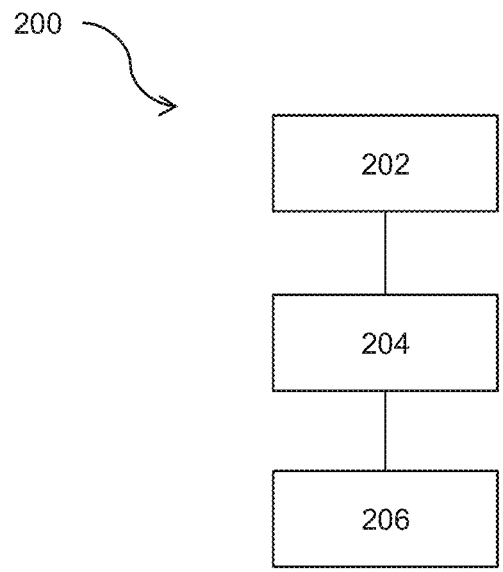
FIG. 2 shows a method for 3D molecular structure estimation used by the system of FIG. 1.
Figure 3:
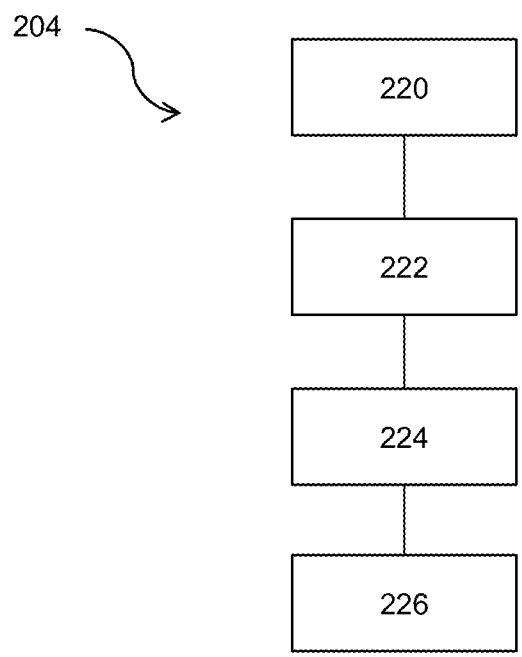
FIG. 3 shows a reconstruction technique of the method for 3D molecular structure estimation.

The system 20 executes a method 200 for 3D molecular structure estimation as illustrated in FIG. 2. The method 200 comprises, at block 202 receiving a set of 2D images of a target specimen from an electron microscope or other imaging system 74, at block 204 carrying out a reconstruction technique to determine a likely molecular structure, and at block 206 outputting the estimated 3D structure of the specimen. The reconstruction technique of block 204 comprises, as illustrated more particularly in FIG. 3: at block 220, establishing a probabilistic generative model of target's density; at block 222, establishing a marginalized likelihood function for the generative model, upon which to perform a MAP estimation of structure; at block 224, using stochastic optimization—such as Stochastic Gradient Descent (SGD), or more specifically Stochastic Average Gradient Descent (SAGD)—to determine which structure is most likely; and, regarding block 226, optionally utilizing importance sampling to efficiently marginalize over unknown pose and position for each particle image, minimizing computational burden.

Figure 4:
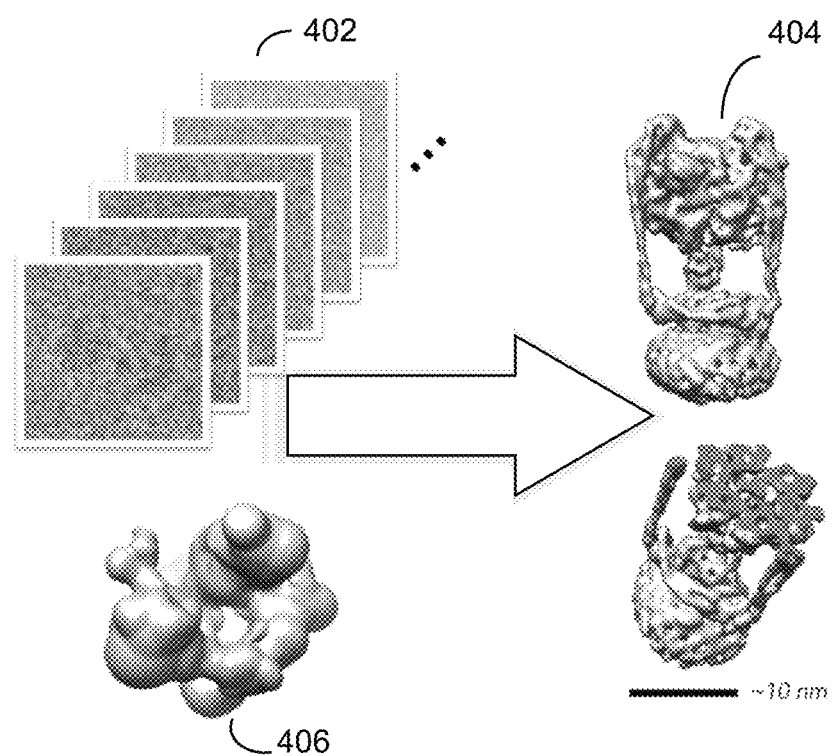
FIG. 4 shows an example application of reconstruction in Cryo-EM.

FIG. 4 illustrates an example application of reconstruction in Cryo-EM according to the method 200. The reconstruction determines a high resolution 3D density estimation 404 of the molecule 406, at sub-nanometer scales of resolution, from a large number of noisy, uncalibrated 2D particle images 402 obtained from cryogenically frozen samples in an electron microscope with a random initialization.

The blocks of method 200, and particularly the reconstruction technique of block 204, will now be described in additional detail in the following with reference to FIGS. 1 to 7, before subsequently describing possible experimental results and testing of the reconstruction technique with reference to FIGS. 8 to 17.

The formulation of a generative model of image formation at block 220 of technique 204 will now be described in the context of cryo-EM. Key elements of the model will be introduced, before clarifying details of the formulation in additional depth. Though the generative formation model for cryo-EM is described herein, the embodiments can be applied to other contexts with corresponding formation models.

Figure 5:
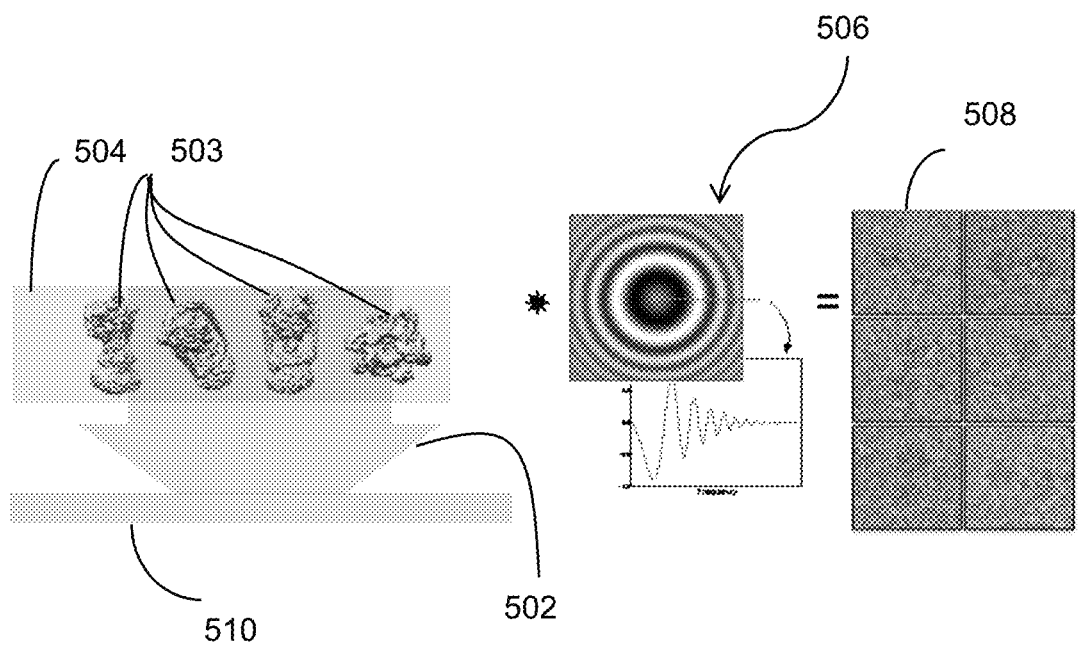
FIG. 5 illustrates image generation with an imaging system and a generative image formation model in Cryo-EM.

FIG. 5 illustrates image generation with an imaging system and a generative image formation model in cryo-EM. An electron beam 502 from imaging system 74 is applied to particles 503 with unknown poses suspended in ice 504, resulting in an orthographic integral projection of the electron density of the specimen on film or a charge coupled device (CCD) 510. This projection is modulated by the Contrast Transfer Function (CTF) shown by element 506 and corrupted with noise, as shown by the corrupted noisy integral projections of particle images 508. The images 508 pictured here showcase the low SNR typical in cryo-EM. Such large amounts of noise are primarily due to very low exposures, necessitated by the sensitive nature of biological specimens. The noise is modelled as independent and identically distributed (IID) and Gaussian. Element 506 of FIG. 5 thus depicts a typical CTF, with periodic phase reversals that imply, among other things, that particle images are not strictly positive. The zeros in the CTF (which completely destroy some spatial information) make estimation particularly challenging, however their locations vary as a function of microscope parameters. These are set differently across particle images in order to mitigate this problem.

In cryo-EM, largely for computational convenience, it is common to express the generative model in the Fourier domain where the key elements have a particularly simple form. The effect of the CTF reduces to modulation in the Fourier domain. Image translation corresponds to a simple phase shift in the Fourier domain. The Fourier Slice Theorem specifies that the Fourier transform of the integral projection of a rotated object yields a slice through the 3D spectrum of the object, in a plane normal to the projection direction. One key benefit of expressing the generative model and likelihood in the Fourier domain is the ease with which the estimation of low-resolution structures can be formulated. This is accomplished by only considering the low-order Fourier terms of the observed images. Computational savings stem from the fact that the number of Fourier coefficients increases quadratically with frequency. The low frequency coefficients also have higher SNR, due in part to CTF attenuation of higher frequencies.

A cryo-EM particle image is assumed to be an orthogonal, integral projection of the 3D target density, V. The 3D pose of the particle in the image, $R \in \mathcal{SO}(3)$, is unknown a priori, as is the 2D position of the particle within the image, $t \in \mathbb{R}^2$. The projection is corrupted by blur and other microscope aberrations, analogous to the effects of defocus in a conventional light camera. Such distortions are characterized by modulation with a CTF in the Fourier domain, denoted $\hat{c}(\omega; \theta)$, where $\omega \equiv (\omega_1, \omega_2)$ represents 2D Fourier coordinates, and $\theta$ denotes the CTF parameters.

As will be formulated below, the generative model in the Fourier domain is given by Eq. 1 as follows:

$$\hat{I}(\omega) = \hat{c}(\omega; \theta) e^{-i2\pi \omega^T t} \hat{V}(\omega_1 n_1 + \omega_2 n_2) + \hat{v}(\omega) \quad (1)$$

where $\hat{I}(\omega)$ denotes 2D Fourier spectrum of the image, $e^{-i2\pi \omega^T t}$ is the phase shift induced by the image translation, $\hat{V}$ is the 3D Fourier spectrum of the target density V, and where $n_1$ and $n_2$ are orthogonal unit vectors that span the plane normal to the viewing direction d. These vectors are given by the rows of the rotation matrix for the 3D pose, i.e. $R = [n_1, n_2, d]^T$. Finally, because the Fourier transform is a linear, unitary transform, the additive, Gaussian image noise remains Gaussian and white in the Fourier domain up to Hermitian symmetry. Given IID mean-zero Gaussian noise with variance $\sigma^2$, the noise in the Fourier coefficients is mean-zero, independent, and complex normal with variance $2\sigma^2$, written $\hat{v}(\omega) \sim CN(0, 2\sigma^2)$.

The formulation of Eq. (1) will now be described in additional depth before describing other blocks of reconstruction technique 204.

The physics of image formation in a transmission electron microscope are described by the Schrödinger equation of quantum mechanics. This partial differential equation would be prohibitively expensive and difficult to work with directly. However, due to the thin nature of samples used in cryo-EM the weak phase object approximation is widely used which results in the linear image formation model described below.

In the weak phase object approximation the electron microscope takes an integral projection of a rotated, translated 3D molecular density. Let V(y) be the 3D density at $y \in \mathbb{R}^3$, and let the transformation from particle coordinate frame to the microscope coordinate frame be $$x_3 = Ry + t_3 \quad (2)$$

where R and $t_3 \equiv (t_1, t_2, t_3)$ are the 3D rotation and translation between coordinate frames, and $x_3 \equiv (x_1, x_2, x_3)$. Without loss of generality we assume the microscope projection is parallel to the $x_3$-axis, and we express the rotation as $R^T = [n_1, n_2, d]$, so the projection direction in the particle frame is d. The integral projection, onto $x \equiv (x_1, x_2)$, is then given by $$P(x; R, t) = \int V(R^T(x_3 - t_3)) dx_3. \quad (3)$$

In addition to the rotation, the orthogonal projection only depends critically on the two components of translation in the plane normal to the projection direction d, i.e., $t \equiv (t_1, t_2)$.

According to the Fourier Slice Theorem, the Fourier transform of an orthogonal projection of V is equivalent to a planar slice through the 3D Fourier spectrum of V. That is, the 2D transform of P(x; R, t), denoted $\hat{P}(\omega; R, t)$, with $\omega \equiv (\omega_1, \omega_2)$ can be written as follows $$\hat{P}(\omega; R, t) \equiv \int P(x; R, t) e^{-i2\pi x^T \omega} dx \quad (4)$$

$$= e^{-i2\pi \omega^T t} \hat{V}(\omega_1 n_1 + \omega_2 n_2) \quad (5)$$

The 2D Fourier spectrum comprises a slice through the 3D spectrum of V and a phase shift. The slice through $\hat{V}$ is on a plane through the origin and normal to d. The phase shift corresponds to the translation between particle and microscope coordinates in the plane normal to d.

The projection P is subject to blur and microscope aberration, which is characterized as the modulation of a contrast transfer function (CTF) in Fourier domain, and denoted $\hat{c}(\omega; \theta)$ with parameters $\theta$. The standard parametric CTF model is derived as part of the weak phase object approximation. The specific form is given by Equation 3 in "Accurate Determination of local defocus and speciment tilt in electron microscopy", *Journal of Structural Biology*, vol. 142, no. 3, pp. 334-47, 2003 by J. A. Mindell and N. Grigorieff, and there exists freely available and widely used software (called CTFFIND3) for parameter estimation of $\theta$. As depicted in FIG. 5, the CTF for an electron microscope oscillates with periodic phase reversals, not typical of traditional light cameras. As a consequence, EM images are not strictly positive, and important frequency structure in the neighborhoods of the zeros is lost. Finally, it is important to note that the locations of zeros vary with experimental settings of the microscope, and are often varied from image to image to ensure that all frequencies are represented among the set of particle images.

The final image is also contaminated by noise, two sources of which are Poisson distributed electron noise, and absorption due to varying thickness of the ice in which the particles are suspended. As is common in the cryo-EM literature, a Gaussian approximation to the Poisson electron noise, and constant ice density in each particle image are assumed. The mean electron noise and the local ice absorption are estimated around the border of each particle image (since particles are roughly centered by the particle picker), and subtracted from the particle images. This is a process commonly known as "floating" in the cryo-EM literature. As a consequence, a mean-zero, white Gaussian noise process with variance $\sigma^2$ and zero density outside the support of the particle are assumed.

Putting the above together, the image in the microscope can be expressed, in the spatial domain, as follows:

$$I(x)=(c*P)(x;\theta,R,t)+v(x), \quad (6)$$

where * denotes convolution, $c(x; \theta)$ is the real-space form of the CTF, and v denotes the white Gaussian noise process.

Thus, in the Fourier domain, as set out above in equation (1):

$$\hat{I}(\omega)=\hat{c}(\omega;\theta)e^{-i2\pi\omega^T t}\hat{V}(\omega_1 n_1+\omega_2 n_2)+\hat{v}(\omega) \quad (1)$$

Because the Fourier transform is unitary, the noise remains additive and Gaussian in the Fourier domain. That is, the distribution of noise at frequency $\omega$ is proportional to a mean-zero, isotropic complex normal random variable with variance $2\sigma^2$. The proportionality and rescaled variance is due to the fact that the noise is constrained to be purely real, resulting in a Hermitian Fourier transform. Note that while the standard definition of a continuous Fourier transform is unitary, most implementations of the discrete Fourier transform are not. In practice the DFT must be rescaled or the equations here must be scaled appropriately.

As described in more detail below with respect to block 222, in practice the density V is discretized to obtain a 3D grid, v, with density represented at each of $D^3$ voxels. $\hat{v}$ denotes the 3D discrete Fourier transform (DFT) of v. Similarly, $\mathcal{I}$ denotes the discrete, observed particle image, with 2D DFT $\hat{\mathcal{I}}$, defined at frequencies $\omega$ in $\Omega \equiv \{(n/D, m/D)\}_{0 \leq n,m<D}$. Given the Gaussian noise model, the Fourier coefficients are independent so the joint likelihood can be written as the product; i.e., providing:

$$p(\hat{\mathcal{I}}|\theta,R,t,v,\sigma^2) \propto \Pi_{\omega \in \Omega} CN(\hat{\mathcal{I}}[\omega];\mu(\omega),2\sigma^2) \quad (7)$$

where $\hat{\mathcal{I}}[\omega]$ denotes the DFT coefficient at frequency $\omega$, and $\mu(\omega)=\hat{c}(\omega; \theta) \ e^{-2\pi i \omega^T t}\hat{v}(\omega_1 n_1+\omega_2 n_2)$ and $CN(\cdot)$ denotes the Complex Normal distribution. To evaluate the Fourier coefficients in Eq. (7) $\hat{v}$ must be interpolated. To do this trilinear interpolation with premultiplication can be used, though more advanced approaches are possible.

One key advantage of expressing the likelihood over Fourier coefficients is that the likelihood to perform low resolution estimation can be easily adapted with significant computational savings. In particular, it is possible to include only low frequency term, e.g., up to a frequency cut-off, $\omega_*$, whereby the computational savings stem from the fact that the number of Fourier coefficients increases quadratically with frequency:

$$p(\hat{\mathcal{I}}|\theta,R,t,V,\sigma^2) \propto \prod_{\substack{\omega \in \Omega \\ \|\omega\|<\omega_*}} CN(\hat{\mathcal{I}}[\omega];\mu(\omega),2\sigma^2) \quad (8)$$

Optimization, as will be described below, entails computation of the gradient of the likelihood with respect to the density v. In so doing, the CTF and pose parameters, and any terms that depend on them, are treated as fixed. Computation of the gradients with respect to $\hat{v}$ is straightforward because of the linearity of interpolation and the image formation model. The gradient with respect to v can then be found through the chain rule to be the (unitary) inverse Fourier transform of the gradient with respect to $\hat{v}$. This is possible because of the linear, unitary nature of the Fourier transform.

Referring now to block 222 of method 200, the establishment of a marginalized likelihood function for the generative model will now be described.

As briefly described above, in practice the target density V is discretized into 3D grid, v, with density represented at each of $D^3$ voxels, the discrete Fourier transform (DFT) of which is denoted $\hat{v}$. Similarly, the observed particle images have $D^2$ pixels, with 2D DFT, $\hat{\mathcal{I}}$, defined on a discrete set of frequencies, $\omega \in \Omega$. Given the white, complex normal noise model, the joint likelihood over the image Fourier coefficients up to a maximum radius in the frequency domain, $\omega_*$, is given by Eq. (8), stated again as follows:

$$p(\hat{\mathcal{I}}|\theta,R,t,V,\sigma^2) \propto \prod_{\substack{\omega \in \Omega \\ \|\omega\|<\omega_*}} CN(\hat{\mathcal{I}}[\omega];\mu(\omega),2\sigma^2) \quad (8)$$

where $\hat{\mathcal{I}}[\omega]$ denotes the image Fourier coefficient at frequency $\omega$, and $\mu(\omega)=\hat{c}(\omega; \theta) \ e^{-i2\pi\omega^T t}\hat{v}(\omega_1 n_1+\omega_2 n_2)$. Computing the mean requires interpolation of the discrete 3D Fourier coefficients and we use trilinear interpolation with premultiplication.

The 3D pose, R, and shift, t, of each particle image are unknown and treated as latent variables which can be marginalized. Similarly in the case of simultaneous reconstruction of multiple 3D structures, the assignment of each 2D image to a particular 3D structure is unknown, and these assignment variables are treated as latent variables as well, though these variables are omitted from the description below for clarity. Assuming R and t are independent of each other and the density v, the following is obtained for the marginal case:

$$p(\hat{\mathcal{I}}|\theta,v,\sigma^2)=\int_{\mathbb{R}^2}\int_{SO(3)}p(\hat{\mathcal{I}}|\theta,R,t,v,\sigma^2)p(R)p(t)dRdt \quad (9)$$

where p(R) is a prior over 3D poses, $R \in SO(3)$, and p(t) is a prior over translations, $t \in \mathbb{R}^2$. In general, nothing is known about the projection direction so p(R) is assumed to be uniform. Particles are picked to be close to the center of each image, so p(t) is chosen to be a broad Gaussian distribution centered in the image.

The double integral in Eq. 9 is not analytically tractable, so numerical quadrature is used. To perform quadrature over 3D pose, it is convenient to use the subgroup structure of $SO(3)$ and parameterize the rotation matrix R in terms of the viewing direction $d \in S$ and an in-plane rotation angle $\psi \in [0, 2\pi)$. To generate a valid quadrature scheme over $SO(3)$, it suffices to combine quadrature schemes over $S$ and $[0,2\pi)$. The conditional probability of an image (i.e., the likelihood) $p(\hat{\mathcal{I}}|\theta,v,\sigma^2)$ is then approximated as follows, providing a marginalized likelihood function of the generative model:

$$\Sigma_{j=1}^{M_d}w_j^d\Sigma_{k=1}^{M_\psi}w_k^\psi\Sigma_{l=1}^{M_t}w_l^t p(\hat{\mathcal{I}}|\theta,R_{j,k},t_l,v,\sigma^2)p(R_{j,k})p(t_l) \quad (10)$$

where $R_{j,k} \equiv R(d_j,\psi_k)$ is the rotation matrix with viewing direction $d_j$ and inplane rotation $\psi_k$, $\{(d_j,w_j^d)\}_{j=1}^{M_d}$ are weighted quadrature points over $S$, $\{(\psi_k,w_k^\psi)\}_{k=1}^{M_\psi}$ are weighted quadrature points over $[0,2\pi)$ and $\{(t_l,w_l^t)\}_{l=1}^{M_t}$ are weighted quadrature points over $\mathbb{R}^2$.

To generate quadrature points over $S$ the approach is as described in "Distributing many points on a sphere," *The mathematical Intelligencer*, vol. 19, no. 1, pp 5-11, 1997 by E. B. Staff and A. B. J. Kuijlaars, which generates a requested number of points $M_d$ which (approximately) uniformly cover $S$ and then use $$w^d = \frac{4\pi}{M_d}.$$

Quadrature points over $[0, 2\pi)$ are generated uniformly, so $$w^\psi = \frac{2\pi}{M_\psi}.$$

Finally, due to the Gaussian form of $p(t)$, Gauss-Hermite quadrature over $\mathbb{R}^2$ is used where the weights $w^t$ are determined by the quadrature scheme.

The accuracy of the quadrature scheme, and consequently the values of $M_d$, $M_\psi$, and $M_t$, are set based on $\omega_*$, the specified maximum frequency considered. The use of higher frequencies requires finer quadrature sampling. Specifically, if $$\alpha = \frac{1}{2} \arccos \frac{(\rho D \omega_*)^2 - 1}{(\rho D \omega_*)^2 + 1}$$

is the angle between discrete wave numbers in Fourier space at a radius of $\omega$, with pixel size $\rho$, then we seek a quadrature scheme which has a maximum angular spacing of approximately $\alpha$. To achieve this we use $$M_d = \left(\frac{3.6}{\alpha}\right)^2 \text{ and } M_\psi = \frac{2\pi}{\alpha}.$$

For $M_t$ we use $M_t = (\rho D \omega_*)^2$ which corresponds to spacing quadrature points at a full period at frequency $\omega_*$.

Referring now to block 224 of technique 204, Stochastic optimization to determine a 3D density estimation will now be described.

Given a set of K particle images, each with CTF parameters and noise levels, $\mathcal{D} = \{(\hat{\mathcal{I}}_i, \theta_i, \sigma_i^2)\}_{i=1}^K$, and assuming conditional independence of the images, the posterior probability of target density $v$ is given by:

$$p(v|\mathcal{D}) \propto p(v) \Pi_{i=1}^K p(\hat{\mathcal{I}}_i|\theta_i, v, \sigma_i^2), \quad (11)$$

where $p(v)$ is a prior over 3D molecular densities.

Several choices of prior are possible, but a simple independent exponential prior is suitable. Specifically, $p(v) = \Pi_{i=1}^{D^3} \lambda e^{-\lambda v_i}$ where $v_i$ is the density of the ith voxel and $\lambda$ is the inverse scale parameter. Other choices of prior are possible as the presented framework allows for any continuous and differentiable prior. Other example priors include an improper (uniform) prior $p(v_i) \propto 1$, and a conditionally autoregressive (CAR) prior $p(v_i|v_{-i}) =$ $$\mathcal{N}\left(v_i \bigg| \frac{1}{26} \sum_{j \in Nbhd(i)} v_j, \sigma_{CAR}^2\right)$$

which is a smoothness prior biasing each voxel towards the mean of its 26 immediate neighbours $Nbhd(i)$.

Estimating the density for reconstruction at block 224 corresponds to finding $v$ that maximizes the posterior in Eq. (11). The density at each voxel is constrained to be positive, as negative density is physically unrealistic. Taking the negative log and dropping constant factors, the optimization problem becomes $\text{argmin}_{v \in \mathbb{R}^{D^3}} f(v)$, $$f(v) = -\log p(v) - \Sigma_{i=1}^K \log p(\hat{\mathcal{I}}_i|\theta_i, v, \sigma_i^2). \quad (12)$$

Optimizing Eq. (12) directly is costly due to the marginalization in Eq. (10) as well as the large number (K) of particle images in a typical dataset. To address these challenges stochastic optimization and optionally importance sampling are utilized. Stochastic optimization methods exploit the large amount of redundancy in most datasets by only considering subsets of data (i.e., images) at each iteration. There are many such stochastic optimization methods, ranging from simple Stochastic Gradient Descent with momentum to more complex methods such as Natural Gradient methods and Hessian-free optimization.

Stochastic Average Gradient Descent (SAGD) is a specific Stochastic optimization technique which may be used at block 224 as it has several important properties. First, it is effectively self-tuning, using a line-search to determine and adapt the learning rate. This is particularly important, as many techniques require significant manual tuning for new objective functions, or datasets. Further, it is specifically designed for the finite dataset case allowing for faster convergence. Finally, SAGD explicitly produces an estimate of the full gradient over the entire dataset, providing a natural way to assess convergence.

The goal at block 224, as stated above is to minimize the negative log posterior in Eq. (12), i.e.:

$$f(V) = -\log p(V) - \sum_{i=1}^K \log p(\hat{\mathcal{I}}_i | \theta_i, V, \sigma_i^2) \quad (13)$$

$$= \sum_{i=1}^K \left[-\frac{1}{K} \log p(V) - \log p(\hat{\mathcal{I}}_i | \theta_i, V, \sigma_i^2)\right] \quad (14)$$

$$= \sum_{i=1}^K f_i(V). \quad (15)$$

At each iteration $\tau$ of the optimization technique, SAGD selects a random particle image, indexed by $k_\tau$, the corresponding objective for which is the log likelihood, denoted, $f_{k_\tau}(v)$. Also, let the gradient of the objective with respect to the 3D density be denoted $g_{k_\tau}(v) \equiv \nabla_v f_{k_\tau}(v)$. As explained above, the objective is continuous and straightforwardly differentiable.

SAGD then computes an update given by $$V_{\tau+1} = V_\tau - \frac{\varepsilon}{L} \sum_{i=1}^K \left[dV_i^\tau - \frac{1}{K} \frac{\partial}{\partial V} \log p(V)\right], \quad (16)$$

where $\varepsilon$ is a base learning rate, L is a Lipschitz constant of the gradient $g_{k_\tau}(v)$ and $$dV_i^\tau = \begin{cases} g_{k_\tau}(V_\tau) & i = k_\tau \\ dV_i^{\tau-1} & \text{otherwise} \end{cases} \quad (17)$$

That is, at iteration $\tau$ the gradient for data point $k_i$ (particle image) is computed, but the gradient update at iteration $\tau$ also uses the most recently computed gradients for all other data points. In the case of reconstruction of multiple 3D structures simultaneously from a single dataset, the update in Eq. (16) becomes a similar series of updates, one for each 3D structure.

In practice, the sum in Eq. (16) is not computed at each iteration. Rather, a running total is maintained and updated as follows:

$$\bar{g}_\tau = \sum_{k=1}^{K} dv_k^\tau \quad (18)$$

$$\bar{g}_{\tau+1} = \bar{g}_\tau - dv_{k_\tau}^\tau + g_{k_\tau}(v_\tau) \quad (19)$$

This technique allows for SAGD to take many steps and make fast progress before a batch optimization algorithm would be able to take even a single step. Further, rather than selecting a single data point at each iteration, a subset of data points (minibatches) is selected and the gradient for the sum of the objective $f_i$ is computed over the entire minibatch. This allows for computational parallelization and helps to reduce the memory required by SAGD. A minibatch size of 200 particle images could be used.

The SAGD technique requires a Lipschitz constant L which is not generally known. Instead it is estimated using a line search algorithm where an initial value of L is increased until the instantiated Lipschitz condition $$f(V) - f(V - L^{-1}dV) < \frac{\|dV\|^2}{2L}$$

is met. The line search for the Lipschitz constant L is only performed once per predetermined number of iterations, e.g. 20 iterations. More sophisticated line search could be performed if desired. A good initial value of L may be found using a bisection search where the upper bound is the smallest L found so far to satisfy the condition and the lower bound is the largest L found so far which fails the condition. In between line searches, L is gradually decreased to try to take larger steps.

Like other stochastic optimization techniques, convergence of SAGD is only guaranteed for convex functions. In practice, while the objective function defined here is non-convex, good performance can be achieved regardless, in keeping with myriad other applications of stochastic optimization. In the convex case, convergence is only assured for values of $$\varepsilon \leq \frac{1}{16}.$$

However larger values at early iterations may be beneficial, and consequently $$\varepsilon = \max\left(\frac{1}{16}, 2^{1-\lfloor \tau/150 \rfloor}\right)$$

is used. To enforce the positivity of density, negative values of v are truncated to zero after each iteration.

Figure 6:
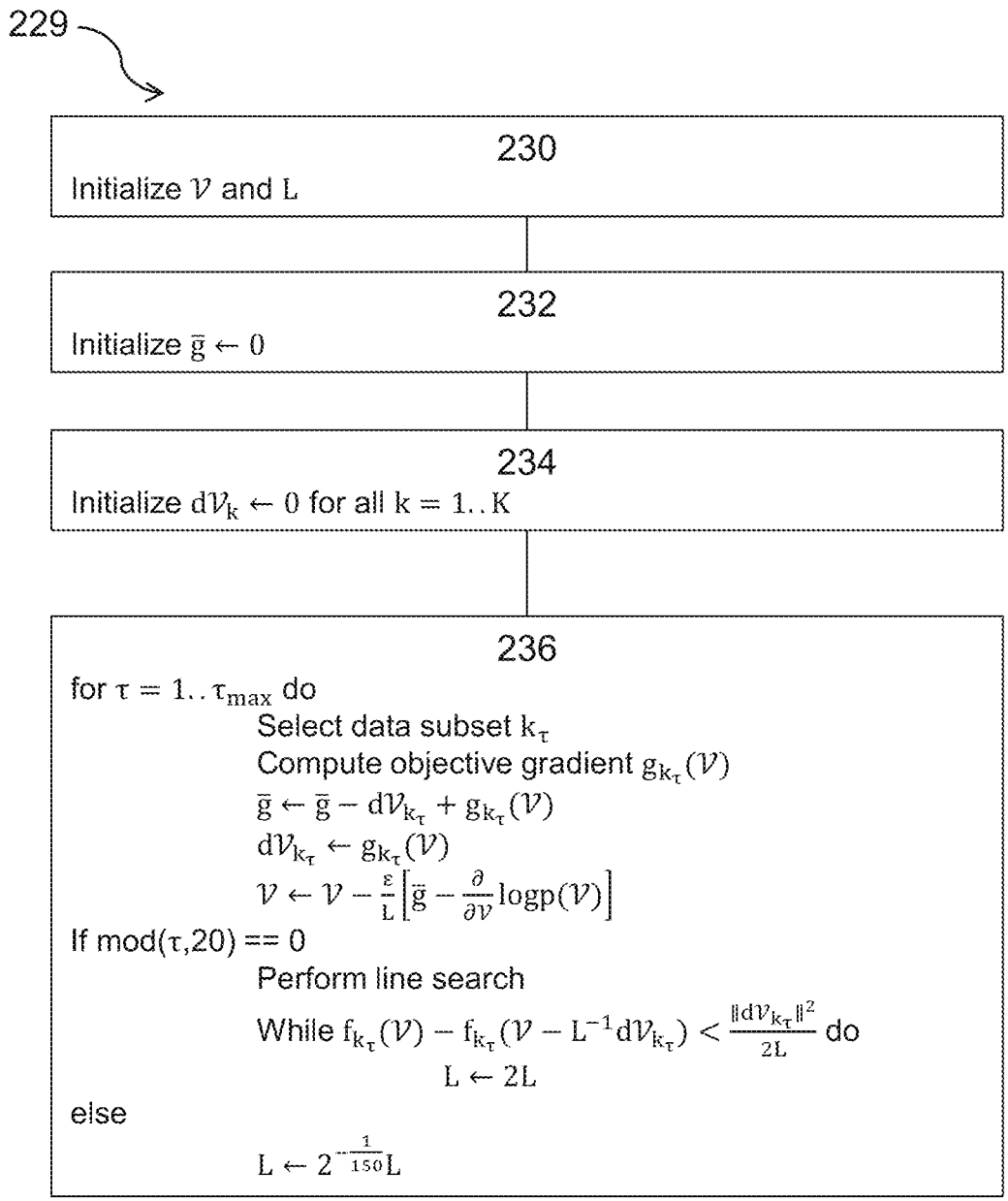
FIG. 6 shows a summary of a technique of Stochastic Gradient Descent of the reconstruction technique.

A summary of the entire SAGD technique 229 carried out at block 224 is shown in FIG. 6. At block 230, the density distribution v and the Lipschitz constant L are initialized. At block 232, the gradient of the objective (log likelihood) with respect to density, $\bar{g} \leftarrow 0$, is initialized. At block 234, the gradient of the density for the data points, $dv_k \leftarrow 0$ for all $k=1 \ldots K$ is initialized.

At block 236, for a first iteration to a max number of iterations, $\tau=1 \ldots \tau_{max}$, a data point (i.e. a particle image) is selected, and the gradient of the objective (log likelihood function) with respect to 3D Density $g_{k_\tau}(v)$ is computed. The gradient and density values are updated as follows: i.e. $\bar{g} \leftarrow \bar{g} - dv_{k_\tau} + g_{k_\tau}(v)$, $dv_{k_\tau} \leftarrow g_{k_\tau}(v)$ and $$V \leftarrow V - \frac{\varepsilon}{L}\left[\bar{g} - \frac{\partial}{\partial V}\log p(V)\right].$$

The gradient update at iteration $\tau$ uses the most recently computed gradients for all other data points, in addition to $k_i$. The sum is not computed at each iteration, rather a running total is maintained and updated. Further, rather than selecting a single data point at each iteration, a subset of data points (minibatches) is selected and the gradient for the sum of the objective $f_i$ is computed over the entire minibatch.

Further at block 236, every 20 iterations a line search for the Lipschitz constant is performed, i.e. if $\mod(\tau,20)=0$, a line search is performed, where an initial value of L is increased until the instantiated Lipschitz condition is met, ergo: while $$f_{k_\tau}(V) - f_{k_\tau}(V - L^{-1}dV_{k_\tau}) < \frac{\|dV_{k_\tau}\|^2}{2L}$$

do $L \leftarrow 2L$. If a line search is not performed, the Lipschitz constant is updated via $$L \leftarrow 2^{-\frac{1}{150}}L$$

until a Lipschitz condition is met.

Referring now to block 226 of technique 204, importance sampling in the reconstruction technique 204 will now be described. Importance sampling enables the reconstruction technique to efficiently marginalize over the unknown pose and position for each particle image, significantly reducing computational burden.

While stochastic optimization allows scaling to a large numbers of images, the cost of computing the required gradient for each image remains high due to marginalization over 3D orientations and 2D shifts in Eq. (10). Intuitively, one could consider randomly selecting a subset of the terms in Eq. (10) and using this as an approximation. This idea is formalized by importance sampling which allows for an efficient and accurate approximation of the discrete sums in Eq. (10). Importance sampling can also be applied directly to the continuous integrals in Eq. (9) but it can be computationally advantageous to have a fixed set of projections and shifts which can be reused across particle images.

To formulate importance sampling, the inner sum from Eq. (10) is first re-expressed as follows $$\phi_{j,k}^{d,\psi} = \sum_{\ell=1}^{M_t} w_\ell^t p_{j,k,\ell} = \sum_{\ell=1}^{M_t} q_\ell^t \left(\frac{w_\ell^t p_{j,k,\ell}}{q_\ell^t}\right) \quad (20)$$

where $p_{j,k,\ell} = p(\hat{y}|\theta, R_{j,k}, t_\ell, \hat{v})p(R_{j,k})p(t_\ell)$ and $q^t \equiv (q_1^t, \ldots, q_{M_t}^t)^T$ is the parameter vector of a multinomial importance distribution such that $\sum_{\ell=1}^{M_t} q_\ell^t = 1$ and $q_\ell^t > 0$. The domain of $q^t$ corresponds to the set of quadrature points in Eq. (10). Then, $\phi_{j,k}^{d,\psi}$ can be thought of as the expected value $$E_\ell\left[\frac{w_\ell^t p_{j,k,\ell}}{q_\ell^t}\right],$$

where l is a random variable distributed according to $q^t$. If a set of $N_t \ll M_t$ random indexes, ${}^t t$, are drawn according to $q^t$, then $$\phi_{j,k}^{d,\psi} \approx \frac{1}{N_t}\Sigma_{\ell \in \mathfrak{I}^t}\frac{w_\ell^t p_{j,\ell}}{q_\ell^t}. \qquad (21)$$

Thus, $\phi_{j,k}^{d,\psi}$ can be approximated by drawing samples according to the importance distribution $q^t$ and computing the average.

Using this approximation, Eq. (10) becomes $$p(\hat{g}\mid\theta,\hat{V}) \approx \sum_{j=1}^{M_d} w_j^d \sum_{k=1}^{M_\psi} w_k^\psi \frac{1}{N_t}\left(\Sigma_{\ell \in \mathfrak{I}^t}\frac{w_\ell^t p_{j,k,\ell}}{q_\ell^t}\right). \qquad (22)$$

Importance sampling can be similarly used for the other summations:

$$p(\hat{g}\mid\theta,\hat{V}) \approx \Sigma_{j \in \mathfrak{I}^d}\Sigma_{k \in \mathfrak{I}^\psi}\Sigma_{\ell \in \mathfrak{I}^t}\frac{w_j^d w_k^\psi w_\ell^t}{N_d N_\psi N_t q_j^d q_k^\psi q_\ell^t}p_{j,k,\ell} \qquad (23)$$

where ${}^t d$ and ${}^t \psi$ are samples drawn from the importance distributions $q^d=(q_1^d,\ldots,q_{M_d}^d)^T$ and $q^\psi=(q_1^\psi,\ldots,q_{M_\psi}^\psi)^T$.

The accuracy of the approximation in Eq. (23) with respect to Eq. (10) is determined in part by the number of samples used, with the error going to zero as the number of samples increases. For $N_d$ we use $s_0 s(q_d)$ samples where $s(q)=(\Sigma_l q_l^2)^{-1}$ is the effective sample size and $s_0$ is a scaling factor. This choice ensures that when the importance distribution is diffuse, more samples are used.

As long as the importance distributions (i.e., $q^t$, $q^d$ and $q^\psi$) are non-zero over their respective domains, the resulting weighted samples are properly weighted and the estimates provided by importance sampling are unbiased. Nevertheless, their estimator variance can arbitrarily poor if the importance distributions are not well chosen.

In the following paragraphs, a particular choice of importance distributions is described, which successfully exploits the iterative nature of the of the algorithm, while ensuring properly weighted samples.

To begin, note that one natural choice for effective importance distributions would be based on the marginal sums $$\phi_j^d = \Sigma_{k=1}^{M_\psi}\Sigma_{l=1}^{M_t}w_k^\psi w_l^t p_{j,k,l} \qquad (24)$$

$$\phi_k^\psi = \Sigma_{j=1}^{M_d}\Sigma_{l=1}^{M_t}w_j^d w_l^t p_{j,k,l} \qquad (25)$$

$$\phi_l^t = \Sigma_{j=1}^{M_d}\Sigma_{k=1}^{M_\psi}w_j^d w_k^\psi p_{j,k,l}. \qquad (26)$$

These sums essentially tell us how significant a particular viewing direction, inplane rotation, or inplane shift is for the quadrature, and thus how strongly it should be sampled.

Unfortunately computing these sums requires as much work as computing Eq. (10) directly.

Figure 7:
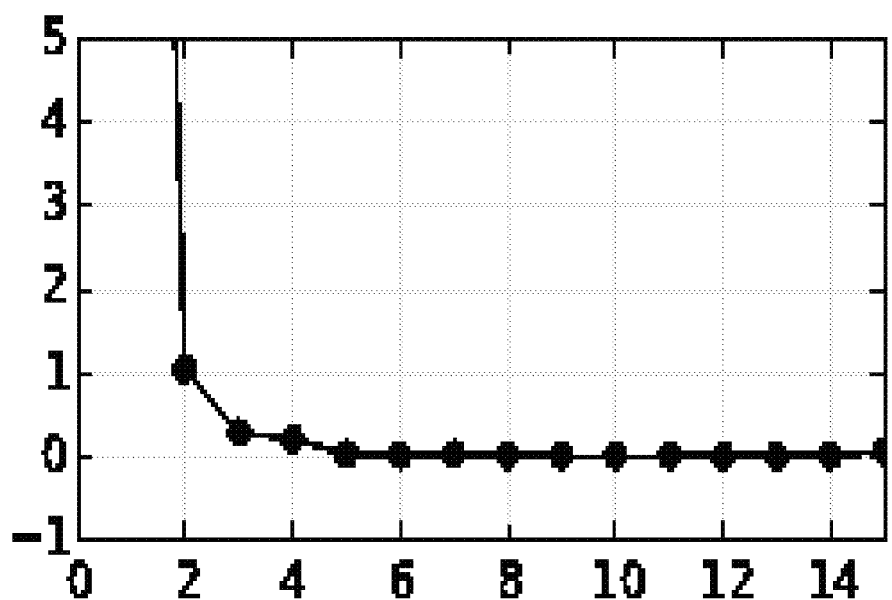
FIG. 7 shows possible KL divergence over the course of epochs during optimization.

To avoid such expense two observations are made. First, once the rough shape of the structure has been determined, the marginal sums do not change dramatically from iteration to iteration of stochastic optimization. Intuitively, once a structure has been coarsely determined, the correct pose and shift for a particular image will not change much as the 3D structure is further updated. This is illustrated in FIG. 7, which illustrates divergence vs. epochs, where, an epoch is an entire pass through the full dataset, while an iteration is a single update of the density using only a small, randomly selected subset of the dataset. A full epoch consists of some number of iterations, roughly equal to K/N where K is the number of images in the dataset and N is the number of images considered at each iteration; K is thus a function of the dataset. Possible results with N=200 are illustrated. In FIG. 7 by the third epoch the KL divergence of $\phi^d$ from one epoch to the next is extremely small. FIG. 7 thus suggests that $\phi$ from the previous epoch may be useful in constructing the importance distribution at the current epoch. Specifically, FIG. 7 illustrates a possible KL divergence (on the y-axis) between the values of $\phi^d$ at the current and previous epochs (on the x-axis) for a thermus dataset. As optimization progresses, the coarse structure of the molecule is quickly determined, and the KL divergence becomes very small by the third epoch. This indicates that the significantly likely poses for each image have stabilized, and so importance sampling can focus quadrature on these regions preferentially, providing significant speedups.

The second observation is that these distributions can also be approximated by importance sampling; i.e., $$\tilde{\phi}_j^d = \Sigma_{k \in \mathfrak{I}^\psi}\Sigma_{\ell \in \mathfrak{I}^t}\frac{w_k^\psi w_\ell^t p_{j,k,\ell}}{N_\psi N_t q_k^\psi q_\ell^t} \qquad (27)$$

$$\tilde{\phi}_k^\psi = \Sigma_{j \in \mathfrak{I}^d}\Sigma_{\ell \in \mathfrak{I}^t}\frac{w_j^d w_\ell^t p_{j,k,\ell}}{N_d N_t q_j^d q_\ell^t} \qquad (28)$$

$$\tilde{\phi}_\ell^t = \Sigma_{j \in \mathfrak{I}^d}\Sigma_{k \in \mathfrak{I}^\psi}\frac{w_j^d w_k^\psi p_{j,k,\ell}}{N_d N_\psi q_j^d q_k^\psi}. \qquad (29)$$

These quantities can be used, computed from the previous iterations, to construct the importance distributions at the current iteration. Further these distributions can be annealed to smooth out sharp peaks.

The actual importance distributions used can be two-component mixture models, comprising a convex combination of a uniform distribution and the approximate marginals from the last epoch. The uniform distribution helps to ensure that the importance distribution is non-zero everywhere. In effect, it encourages search over the entire space, while the other component of the mixture focuses search in regions that previously had high probability. Dropping the superscripts for clarity, let ${}^t$ be the set of samples evaluated at the previous iteration and $\phi_i$ be the computed values for $i \in {}^t$. Then the importance distribution used at the current iteration is $$q_j = (1-\alpha)Z^{-1}\Sigma_{i \in {}^t}\tilde{\phi}_i^{1/T}K_{i,j}+\alpha\psi \qquad (30)$$

where $\psi=M^{-1}$ is the uniform distribution, $\alpha$ is the mixing proportion with the uniform distribution, T is an annealing parameter, $K_{i,j}$ is a kernel evaluated between quadrature points i and j, and $Z=\Sigma_j\Sigma_{i \in {}^t}\tilde{\phi}_i^{1/T}K_{i,j}$ is a normalization constant. The values for $\alpha=\max(0.05, 2^{-0.25\lfloor\tau_{prev}/50\rfloor})$ and $T=\max(1.25, 2^{10.0/\lfloor\tau_{prev}/50\rfloor})$ are set so that at early iterations, when the underlying density is changing, we rely more heavily on the uniform $\psi$.

The kernel K is used to diffuse probability around quadrature points as neighbouring points are more likely to be useful. It also enables smooth transitions between resolutions of quadrature points. For the specific kernels, we use a squared exponential kernel for the shifts and an exponential kernel for the projection directions and in-plane rotations. That is:

$$K_d(d_i, d_j) = \exp(\kappa_d d_i^T d_j) \quad (31)$$

$$K_\psi(\psi_i, \psi_j) = \exp(\kappa_\psi \cos \angle(\psi_i, \psi_j)) \quad (32)$$

$$K_t(t_i, t_j) = \exp(-\kappa_t \|t_i - t_j\|^2) \quad (33)$$

where $$\kappa_d = \frac{\log 4}{1 - \cos r_d}, \kappa_\psi = \frac{\log 2}{1 - \cos r_\psi}, \text{ and } \kappa_t = \frac{1}{2r_t^2}$$

are kernel bandwidth parameters and $\angle(\psi_i, \psi_j)$ is the angular difference between $\psi_i$ and $\psi_j$. The bandwidth parameters are set based on the resolution of the quadrature schemes where $r_d$ and $r_\psi$ are the angular distances between projection directions and in-plane rotations respectively and $r_t$ is the distance between translation quadrature points.

Possible experimental results and testing methodologies for verifying the reconstruction technique of block 204 will now be described with reference to FIGS. 8 to 18.

Figure 8:
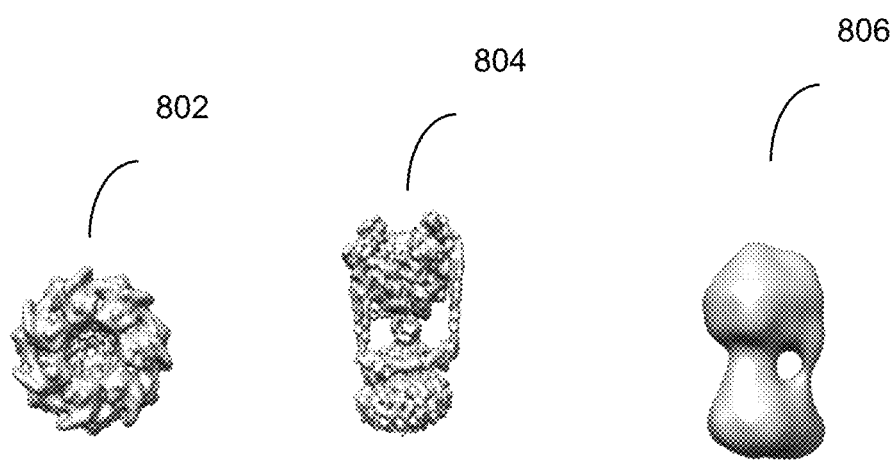
FIG. 8 shows possible structures for reconstruction.

The reconstruction technique of block 204 could be applied to different experimental and synthetic datasets, and experiments could be initialized using randomly generated densities. Two possible experimental datasets include ATP synthase from the *Thermus thermophilus* bacteria, a large transmembrane protein complex, and bovine mitochondrial ATP synthase, with CTF, signal-to-noise and other parameters being given. A synthetic dataset could be synthesized by taking an existing structure from the Protein Data Bank, e.g. GroEL-GroES-(ADP)7, and generating random projections according to the generative model, with parameters being set to plausible values. FIG. 8 shows possible structures, where block 802 relates to GroEL-GroES, 804 relates to Thermus ATPase, and 806 relates to Bovine ATPase. For testing, the maximum frequency considered could be gradually increased from an initial value of $\omega_*=1/40$ Å to a maximum of $\omega_*=1/9$ Å (i.e., a wavelength of 9 Å). Optimizations could be run until a maximum resolution was reached and the average error on a held-out set of 200 particle images stopped improving, e.g. around 5000 iterations.

Figure 9:
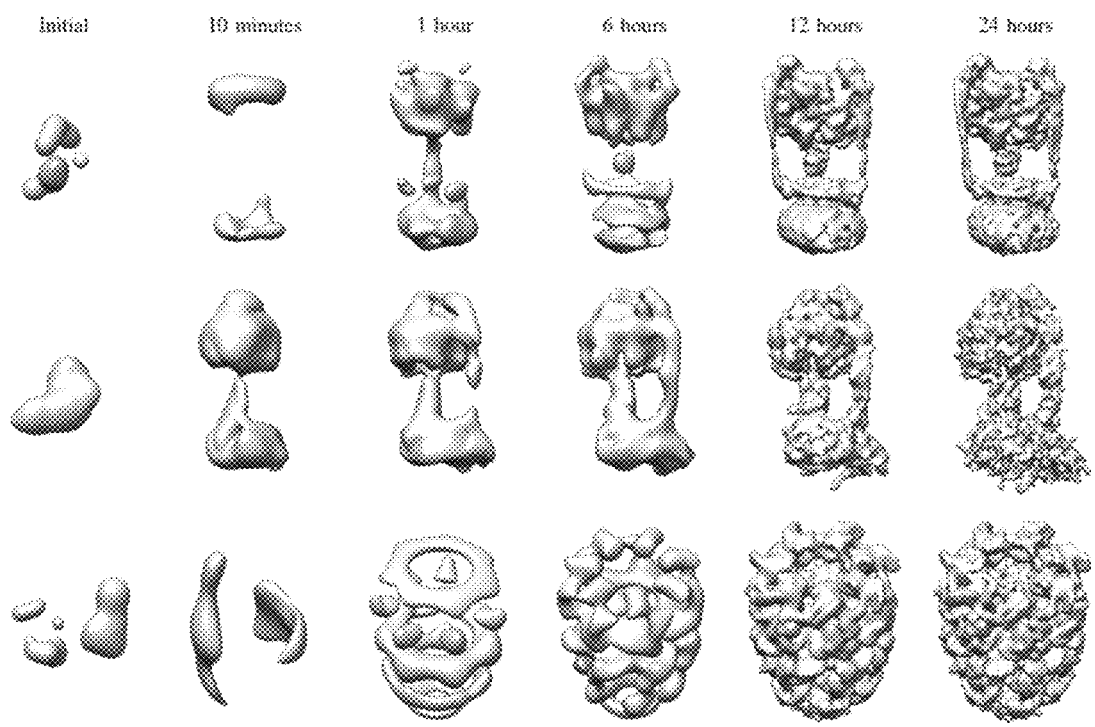
FIG. 9 shows possible estimated structures of targets at several times during a reconstruction.

FIG. 9 shows possible estimated structures at several times during a possible reconstruction exercise utilizing the reconstruction technique of block 204 for the structures illustrated in FIG. 8. The top row relates to thermus, the middle row Bovine, and the bottom row GroEL-GroES datasets. Initializations could be generated randomly as a sum of spheres. Note that within an hour of computation, the gross structure could already be well determined, after which fine details would emerge gradually.

Figure 10:
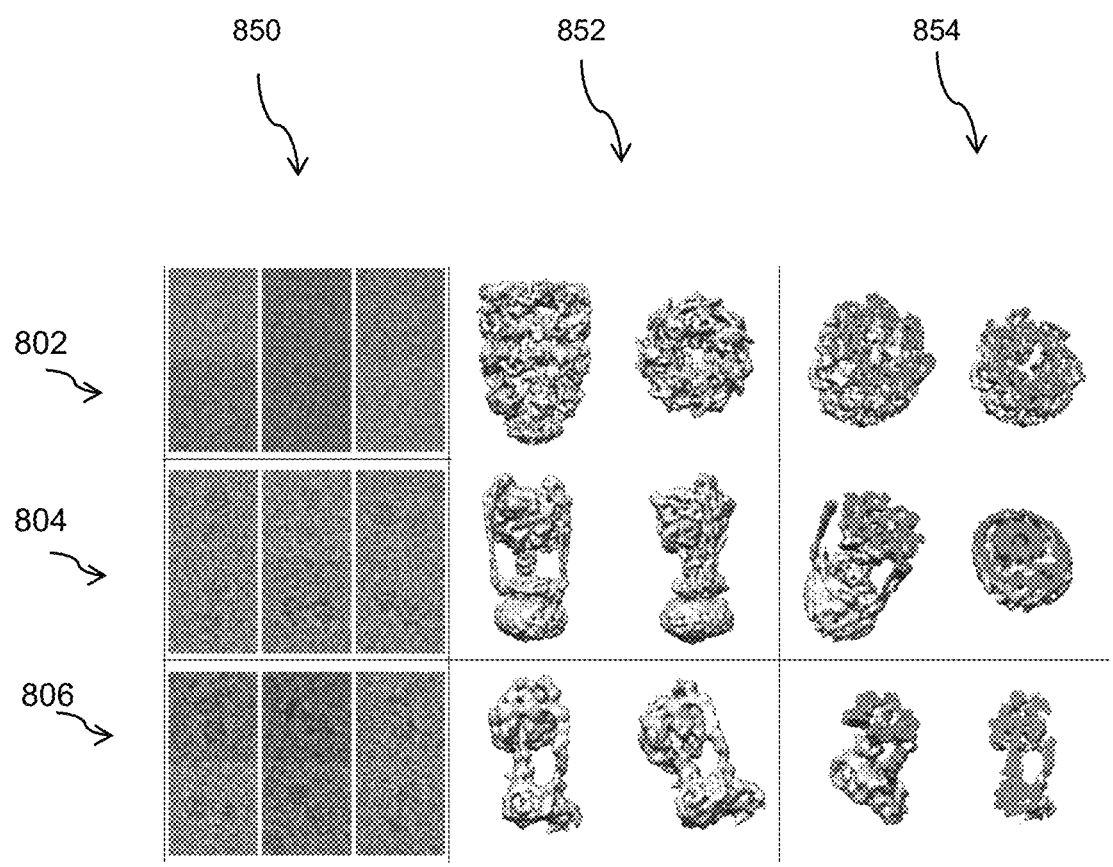
FIG. 10 shows possible results of a reconstruction exercise, as well as the original particle images and slices through the 3D density reconstructions.

FIG. 10 shows possible results of the reconstruction, along with an iso-surface and slices of the final estimated density. Computing these reconstructions could take less than 24 hours. FIG. 10 shows sample particle images 850, an isosurface of the reconstructed 3D density 852 and slices through the 3D density with shading indicating relative density at 854, for GroEL-GroES 802, *Thermus thermophilus* ATPase 804 and bovine mitochondrial ATPase 806. Reconstructions could take a day or less on a single 16 core workstation.

Figure 11:
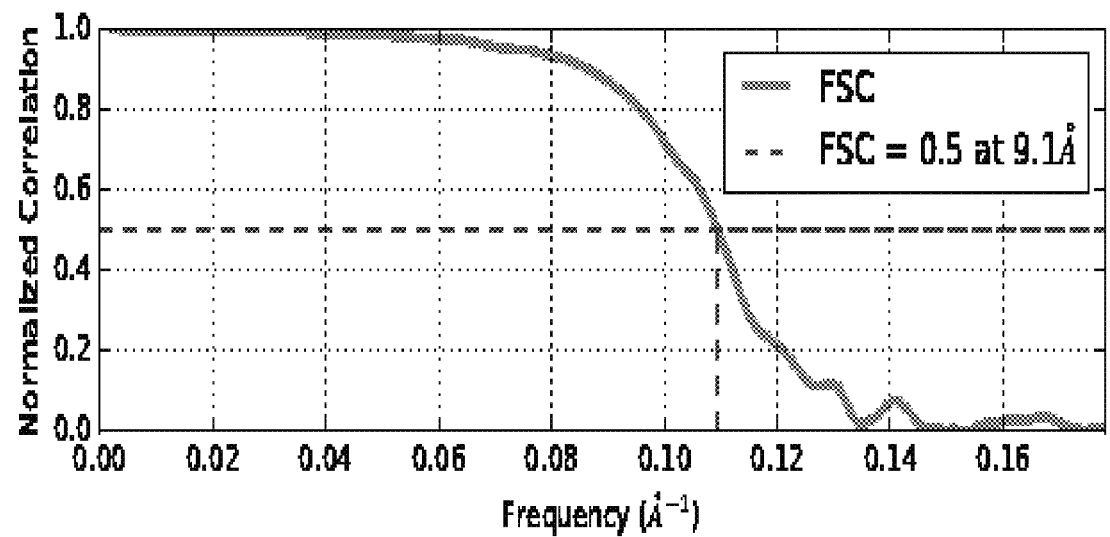
FIG. 11 shows possible results of Fourier Shell Correlation between the estimated structure and the ground truth for an example synthetic dataset of GroEL-GroES.

With regard to quantitative evaluation, traditionally, the cryo-EM field has used the Fourier Shell Correlation (FSC) to measure the similarity between two 3D densities. FSC is the normalized cross-correlation, computed using the 3D Fourier coefficients of the density in shells of fixed frequency magnitude. This produces a function of frequency that is typically near one for low frequency shells and decreases for higher frequency shells, as similarity between the densities decreases. The point at which the correlation drops below half is nominally defined as the resolution to which to two densities match. FSC requires that the two densities being compared are aligned. If this is not the case, an optimal alignment can be computed by maximizing the (overall) normalized cross-correlation using a simplex based search. Ground-truth is rarely available for cryo-EM which makes it difficult to assess the accuracy of estimated densities. However, for a synthetic dataset, like for GroEL-GroES, a comparison can be made against the ground truth structure to determine whether the estimated structure is accurate. A possible FSC curve for the GroEL-GroES dataset is shown in FIG. 11, which provides a table showing possible results of Fourier Shell Correlation between the estimated structure and the ground truth for an example synthetic dataset of GroEL-GroES. In this case it can be seen that the estimated resolution of 9.1 Å is consistent with the highest frequency of coefficients that might be considered, which was 9 Å. The estimated resolution of 9.1 Å would thus be consistent with the highest frequencies considered, i.e., the largest value of $\omega_*$. Power in the solved structures above this frequency is due to the influence of non-negativity and the prior.

Figure 12:
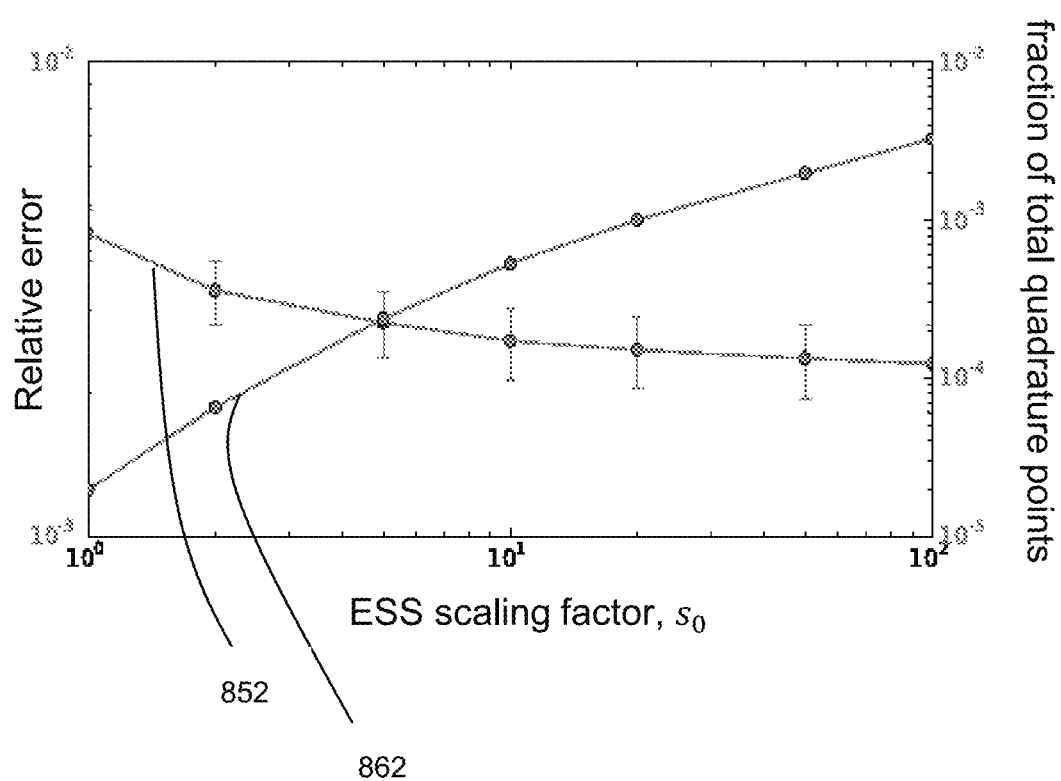
FIG. 12 shows relative Root Mean Square Error (RMSE) along the left axis, and fraction of total quadrature points (along the right axis) as a function of a scaling factor.

Additionally, to validate the importance sampling approach of block 226, error made in computing log $p(\hat{\mathcal{J}}|\theta,\hat{v})$ could be evaluated by comparing results using importance sampling as compared to computing the exact sum in Eq. (10) without importance sampling. A possible error plot is shown in FIG. 12, along with the fraction of quadrature points used at various values of $s_0$. Specifically, FIG. 12 provides a table showing relative Root Mean Squared Error (RMSE) 860 along the left axis, and fraction of total quadrature points used in computing log $p(\hat{\mathcal{J}}|\theta,\hat{v})$ 862 (along the right axis) as a function of the ESS scaling factor, $s_0$ (horizontal axis). Note the log-scale of the axes. Error bars represent the variance over a population of 100 individual images. Based on these plots, a factor of $s_0=10$ could be selected as a trade-off between accuracy and speed achieving a relative error of less then 0.1% while still providing significant speedups.

Figure 13:
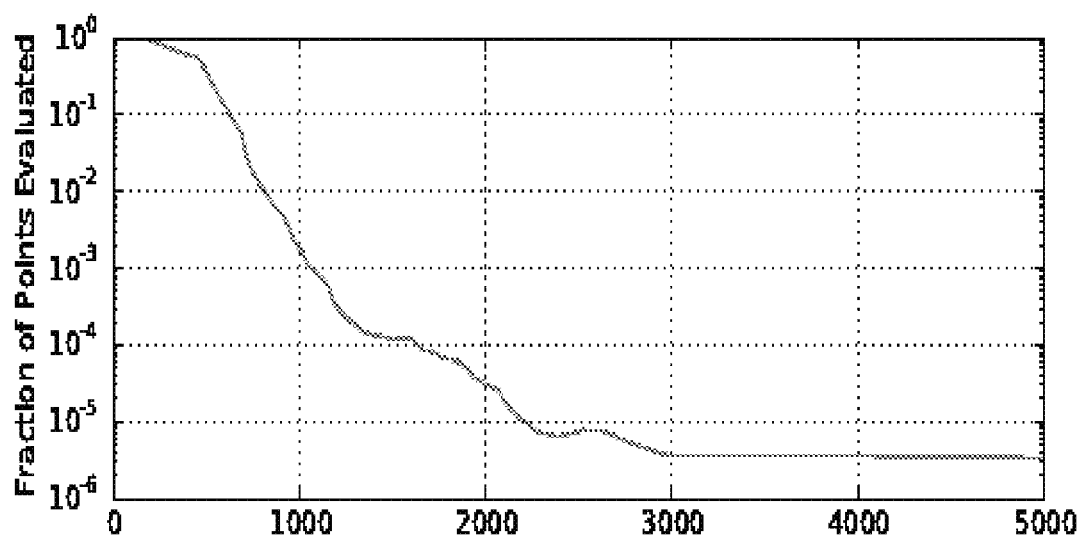
FIG. 13 shows possible results of a fraction of naive quadrature points evaluated on average during optimization, when using importance sampling.

Further, to see just how much of a speedup importance sampling provides in practice, the fraction of quadrature points evaluated during optimization could be determined, as illustrated in FIG. 13. FIG. 13 shows possible results of the fraction of naive quadrature points evaluated on average during optimization, when using importance sampling. As shown initially all quadrature points may be evaluated, but as optimization progresses, and the density becomes better determined, importance sampling yields larger and larger speedups. At the full resolution, importance sampling could provide more than a 100,000-fold speedup.

Figure 14:
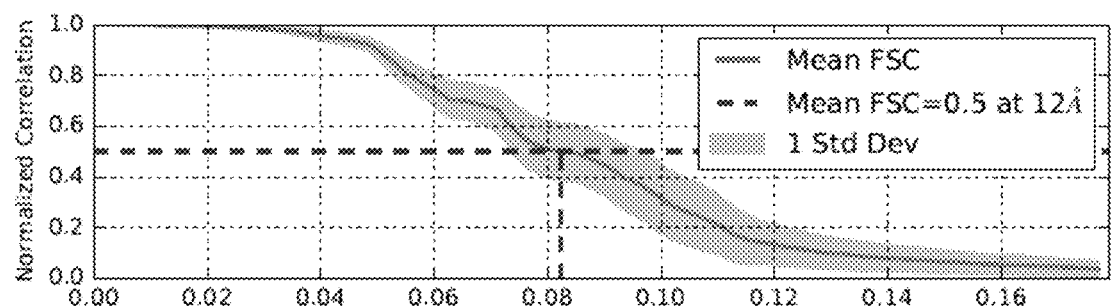
FIG. 14 shows possible Fourier Shell Correlation mean and standard deviation for pairs of density maps.
Figure 15:
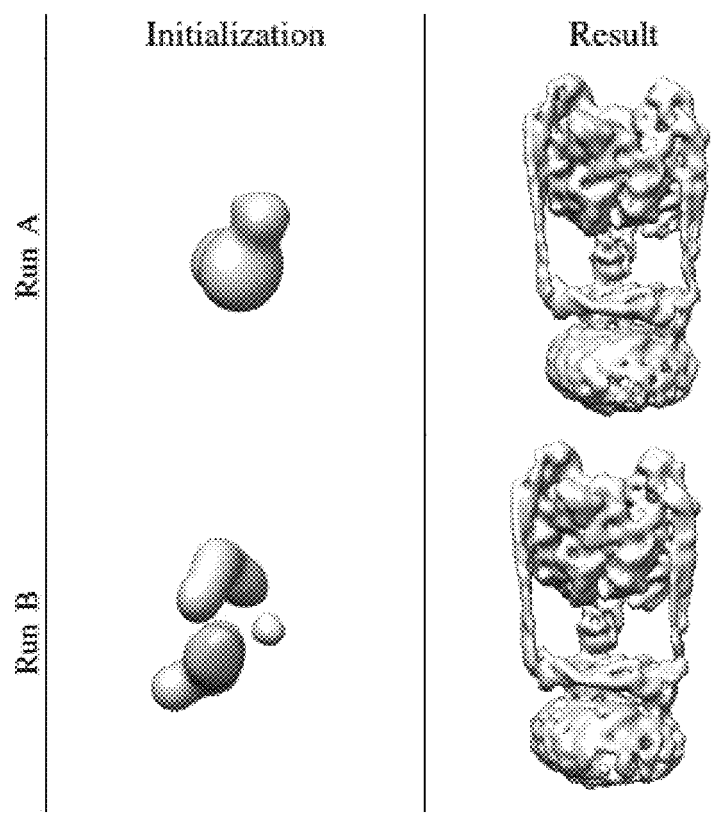
FIG. 15 shows results from two individual runs of reconstruction.

To demonstrate the robustness of the reconstruction technique to initialization, different random initial densities could be generated and run with the datasets. Qualitatively, it might be determined that the resulting structures from all runs are similar to one another. To assess quantitative similarity, the aligned FSC could be computed between all pairs of the final density maps. As mentioned above, FSC curves measure consistency of density maps as a function of resolution. FIG. 14 shows possible FSC mean and standard deviation for pairs of density maps. More specifically, FIG. 14 shows a possible comparison of multiple restarts with the same Thermus data using different randomly generated initializations, illustrating average Fourier Shell Correlation between independent runs. The example curve indicates that the densities are extremely close in structure all the way down to a resolution of 12 Å on average, which is approximately half the Nyquist frequency, meaning that the results are consistent to approximately 2 pixels. This indicates that the different random initializations are effectively converging to very similar solutions. This would demonstrate the robustness of the method to random initializations. FIG. 15 shows example initializations and results from two individual runs.

Additionally, to compare this reconstruction technique 204 to others, especially its sensitivity to initialization, well-known, state-of-the-art approaches for structure determination could be used as comparators. The first could be a standard iterative projection matching scheme where images are matched to an initial density through a global cross-correlation search. The density could then reconstructed based on these fixed orientations and the process is iterated. The second benchmark could be the RELION™ package. Publicly available code could be used for the comparisons, utilziing, for example the thermus dataset and initializing using the same randomly generated density. Each method could be run for a number of iterations roughly equivalent in terms of CPU time to the iterations used by in testing the reconstruction technique 204.

Figure 16:
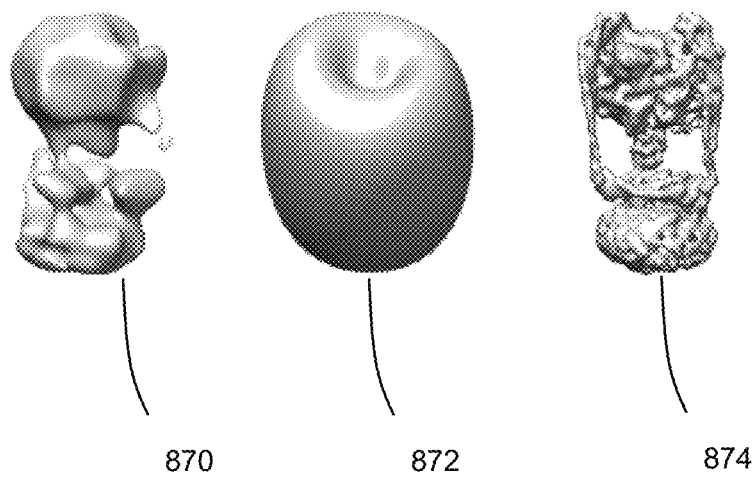
FIG. 16 shows possible results of iterative projection matching and reconstruction with different techniques.

FIG. 16 shows possible results of iterative projection matching and reconstruction at 870, reconstruction by RELION™ at 872, and reconstruction by technique 204 at 874. The reconstruction technique 204 is shown to be able to determine the correct structure while projection matching and RELION™ both become trapped in poor local optima. Both approaches are shown to clearly determine an incorrect structure, and appear to have converged to a local minimum if no further progress is made beyond that point. It should be noted that projection matching and RELION™ are not recommended to be used without a good initialization. The illustrated possible results would support this recommendation as neither approach is shown to converge from a random initialization. In practice, however, it is difficult to construct good initializations for molecules of unknown shape, giving the reconstruction technique 204 a significant advantage.

Figure 17:
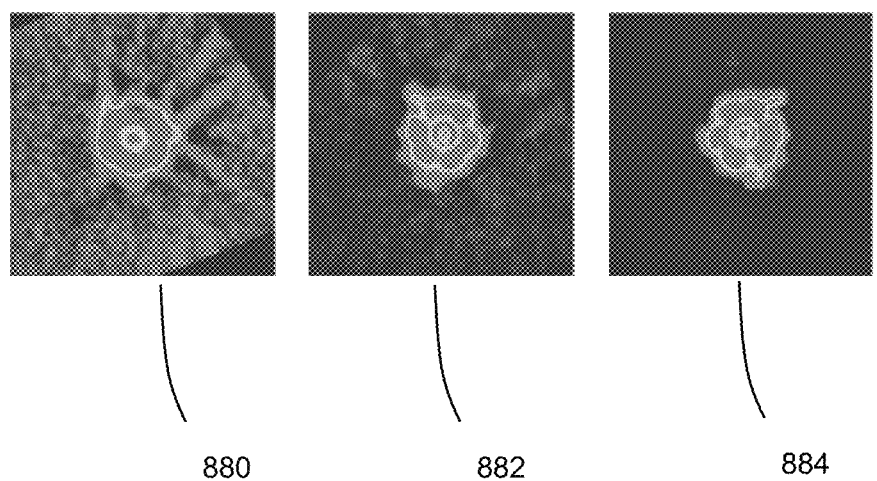
FIG. 17 shows possible results of slices through resulting density reconstructions utilizing different priors.

The above results and discussion of technique 204 used an exponential prior for the density at the voxels of $v_i$, however the presented framework allows for any continuous and differentiable prior. Accordingly, other priors could be explored, such as an improper (uniform) prior, $p(v_i) \propto 1$, and a conditionally autoregressive (CAR) prior $p(v_i|v_{-i})=$ $$\mathcal{N}\left(v_i \Big| \frac{1}{26} \sum_{j \in Nbhd(i)} v_j, \sigma^2_{CAR}\right)$$

which is a smoothness prior biasing each voxel towards the mean of its 26 immediate neighbours Nbhd (i). Possible results of slices through the resulting density reconstructions on thermus under these priors are shown in FIG. 17. Darker shading corresponds to small or zero density and lighter shading corresponds to high density. With an improper uniform prior (shown at 880), there is significant noise visible in the background. This noise is somewhat suppressed with the CAR prior (shown at 882) however the best results are clearly obtained using the exponential prior which suppresses the background noise without smoothing out internal details (shown at 884). According to these possible results, the exponential prior thus does the best job of suppressing noise in the background without oversmoothing fine details within the structure.

In brief summary of the above, the reconstruction technique of block 204 provides a method for estimation of 3D structure, formulating the reconstruction problem as one of stochastic optimization to perform MAP estimation in a probabilistic generative model, given the 3D electron density of the molecule. 3D pose and 2D position of the particle in each image are treated as unknown, latent variables. Stochastic optimization is employed to cope with large-scale datasets and provide robustness to poor initial 3D structure estimates. Importance sampling can be used to efficiently marginalize over the unknown pose and position for each particle image. The approach is efficient, and may provide low resolution density estimates in just a few hours. The stochastic optimization technique is insensitive to initialization, allowing the use of random initializations. Further, a sampling scheme is described that dramatically reduces the computational costs associated with high resolution reconstruction. This may lead to decreased computational time by orders of magnitudes, allowing structures to be determined in a day on a modern CPU workstation. The technique is flexible, allowing parts of the model to be changed and improved without impacting the overall framework.

Although the invention has been described with reference to certain specific embodiments, various modifications thereof will be apparent to those skilled in the art without departing from the spirit and scope of the invention as outlined in the claims appended hereto.

For example, though the Gaussian approximation to the Poisson noise model (used in relation to the generative model of block 220) is well motivated, there may be correlations in the noise. This suggests that a coloured noise model may be applied.

Further, regarding optimization at block 224, while SAGD is suitable, more efficient stochastic optimization methods are possible which exploit the problem structure to a greater degree. This could recover even higher resolution structures as the Hessian matrix can be shown to become poorly conditioned, meaning that first-order optimization methods will likely struggle to reach the optimal solution.

Further, as described briefly above, the generative model of block 220 can be extended in a straightforward way to the case of heterogeneous datasets that contain 2D particle images each containing the image of one of several possible 3D structures. In this embodiment the method comprises determining a probabilistic model of 3D structures of the targets; and optimizing the probabilistic model utilizing stochastic optimization to determine the most likely 3D structure of each target. The variables of MAP estimation include the voxels of all 3D structures that are simultaneously estimated, and stochasic optimization can be employed in the same way as described, providing updates to all 3D structures at each iteration. The assignments of each 2D particle image to a particular 3D target are treated as unknown latent variables. Where multiple 3D targets are simultaneously reconstructed from a single set of 2D particle images, the number of 3D targets may be specified prior to the reconstruction.

The invention claimed is:

1. A system for producing a 3D molecular structure reconstruction from a set of 2D Cryo-electron microscope particle images of at least one target to determine estimated 3D structures for the at least one target, the system comprising:
- a storage unit for storing the set of 2D Cryo-electron microscope particles images of the at least one target; and
- a processing unit to:
  - determine a probabilistic generative model of a density distribution of the at least one target from the stored set of 2D Cryo-electron microscope particles images, the probabilistic generative model comprising:
    - a modulation by a contrast transfer function of the particle images;
    - a phase shift induced by particle image translation; and
    - a 3D spectrum of a 3D density for each respective target, the 3D density discretized on a 3D grid for each respective target, the 3D spectrum having coefficients in the Fourier domain;
  - determine a marginalized likelihood function over the coefficients in the Fourier domain for the probabilistic generative model;
  - perform a maximum-a-posteriori (MAP) density estimation of structure on the probabilistic generative model
  - optimize the probabilistic generative model utilizing Stochastic Average Gradient Descent (SAGD) to determine a most likely 3D structure of each target; and
  - output the optimized probabilistic generative model representing the estimated 3D structure of each target.

2. The system of claim 1, wherein the most likely 3D structure comprises an estimate of the 3D density of each target.

3. The system of claim 1, wherein the 3D pose and 2D position of each target in the respective particle images are treated as unknown latent variables.

4. The system of claim 1, wherein the probabilistic model comprises a likelihood function marginalized over 3D orientations and 2D shifts of the at least one target in the particle images, the marginalization being effected on a generative model of the 3D density of the at least one target.

5. The system of claim 1, wherein utilizing Stochastic Average Gradient Descent comprises, iteratively, selecting a mini batch of particle images, computing a gradient of the log of the likelihood function with respect to 3D density for the mini batch of particle images, and adding the gradient to a running total.

6. The system of claim 5, wherein after a predetermined number of iterations have elapsed a line search is computed for tuning the optimization.

7. The system of claim 1, wherein optimizing the probabilistic model utilizing Stochastic Gradient Descent further comprises applying importance sampling to efficiently marginalize over the unknown pose and position of each particle image.

8. The system of claim 7, wherein importance sampling comprises applying two-component mixture models as importance distributions.

9. The system of claim 8, wherein importance sampling comprises selecting particle images according to the importance distributions.

10. The system of claim 1, wherein the size of the at least one target is as small as 100 Angstroms in diameter.

11. The system of claim 1, wherein at least one target comprises a protein or virus.

12. The system of claim 1, wherein the at least one target comprises two or more targets, and the set of 2D Cryo-electron microscope particles images is heterogeneous, whereby each image provides an image of the 3D structure of one of the two or more targets.

13. The system of claim 1, wherein optimizing the probabilistic generative model by the processing unit comprises:
- initializing the density distribution;
- initializing a gradient of the likelihood function;
- initializing a gradient of the density; and
- iteratively, for each data point in a set of data points on the particle images, determining the gradient of the likelihood function with respect to density.

14. The system of claim 13, wherein determining the gradient of the likelihood function with respect to density comprises updating a sum with previously determined gradients of the likelihood function for other data points.

15. The system of claim 13, wherein optimizing the probabilistic generative model further comprises determining a Lipschitz constant using a line search algorithm.

* * * * *